United States Patent
Zhang et al.

(10) Patent No.: US 9,353,049 B2
(45) Date of Patent: May 31, 2016

(54) PREPARATION METHOD FOR RIVASTIGMINE, INTERMEDIATES THEREOF, AND PREPARATION METHOD FOR SAID INTERMEDIATES

(75) Inventors: Fuli Zhang, Shanghai (CN); Zhezhou Yang, Shanghai (CN); Chunbo Yang, Shanghai (CN); Daoxin Chen, Zhejiang (CN); Zhiqing Yang, Zhejiang (CN); Rentong Sun, Zhejiang (CN); Hua Bai, Zhejiang (CN)

(73) Assignees: Zhejiang Hisun Pharmaceutical Co., Ltd., Zhejiang (CN); Shanghai Institute of Pharmaceutical Industry, Shanghai (CN)

( * ) Notice: Subject to any disclaimer, the term of this patent is extended or adjusted under 35 U.S.C. 154(b) by 198 days.

(21) Appl. No.: 14/118,411

(22) PCT Filed: May 16, 2012

(86) PCT No.: PCT/CN2012/075555
§ 371 (c)(1),
(2), (4) Date: Nov. 18, 2013

(87) PCT Pub. No.: WO2012/155834
PCT Pub. Date: Nov. 22, 2012

(65) Prior Publication Data
US 2014/0073809 A1    Mar. 13, 2014

(30) Foreign Application Priority Data
May 18, 2011   (CN) .......................... 2011 1 0133663

(51) Int. Cl.
| C07C 269/04 | (2006.01) |
| C07C 269/06 | (2006.01) |
| C07C 271/44 | (2006.01) |
| C07C 215/66 | (2006.01) |
| C07C 217/58 | (2006.01) |
| C07C 309/04 | (2006.01) |

(52) U.S. Cl.
CPC ............. *C07C 271/44* (2013.01); *C07C 215/66* (2013.01); *C07C 217/58* (2013.01); *C07C 269/04* (2013.01); *C07C 269/06* (2013.01); *C07C 309/04* (2013.01); *C07B 2200/07* (2013.01)

(58) Field of Classification Search
CPC ........................... C07C 269/04; C07C 269/06
See application file for complete search history.

(56) References Cited

U.S. PATENT DOCUMENTS

| 5,602,176 A | 2/1997 | Enz |
| 2010/0286437 A1 | 11/2010 | Zhang et al. |

FOREIGN PATENT DOCUMENTS

| CN | 101910110 A | 12/2010 |
| EP | 2 233 465 A1 | 9/2010 |
| GB | 2 409 453 A | 6/2005 |
| WO | 2004/037771 A1 | 5/2004 |
| WO | 2007/025481 A1 | 3/2007 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
International Search Report mailed Aug. 30, 2012; PCT/CN2012/075555.

* cited by examiner

*Primary Examiner* — Paul A Zucker
(74) *Attorney, Agent, or Firm* — Ladas & Parry LLP

(57) ABSTRACT

The present invention provides a preparation method for (S)-3-(1-(dimethylamino)ethyl)phenyl ethyl(methyl)carbamate, preparation methods for intermediates (S)-1-(3-methoxyphenyl)-N,N-dimethyl-N—((S)-1-phenylethyl)ethanaminium, (S)-1-(3-hydroxyphenyl)-N,N-dimethyl-N—((S)-1-phenylethyl)ethanaminium and (S)-1-(3-(ethyl(methyl)carbamoyloxy)phenyl)-N,N-dimethyl-N—((S)-1-phenylethyl)ethanaminium, as well as a method for using (S)-1-(3-(ethyl(methyl)carbamoyloxy)phenyl)-N,N-dimethyl-N—((S)-1-phenylethyl)ethanaminium to prepare rivastigmine which can be used for the treatment of Alzheimer's disease.

12 Claims, No Drawings

PREPARATION METHOD FOR RIVASTIGMINE, INTERMEDIATES THEREOF, AND PREPARATION METHOD FOR SAID INTERMEDIATES

CROSS-REFERENCES TO RELATED APPLICATION

The present application claims priority under 35 U.S.C. 119(a) to Chinese application number 201110133663.7 entitled "Rivastigmine's preparation method, its intermediates and the intermediates' preparation method" which was submitted to the State Intellectual Property Office of the People's Republic of China on May 18, 2011, which is incorporated by reference in its entirety as if set forth in full.

TECHNICAL FIELD

This invention relates to pharmaceutical synthesis field, in particular it involves the preparation method for a(S)-3-(1-(dimethylamino)ethyl)phenyl ethyl(methyl)carbamate and its tartaric acid salt (i.e., formula I compounds).

BACKGROUND OF THE DISCLOSURE

Rivastigmine is used in the treatment of Alzheimer's disease which selectively inhibits acetylcholinesterase. Its structure is as shown formula (I) below:

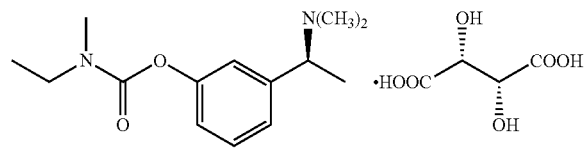

I

U.S. Pat. No. 5,602,176 and GB2409453 released for the first time the synthesis methods for rivastigmine: first, prepare racemic rivastigmine through a series of reactions, and then salify it with (+)-Di-p-toluoyl-D-tartaric acid monohydrate (D-(+)-DTTA); then it goes through five times of recrystallization to get rivastigmine with an optical purity greater than 99%, and the resolution yield is only 26.8% WO2004037771 discloses a method to resolve rivastigmine intermediates: use S-(+)-camphorsulfonic acid to resolve racemic intermediate (RS)-3-(1-(dimethylamino)ethyl)phenol, let it go through three times of recrystallization and purification to obtain optically pure(S)-3-(1-(dimethylamino)ethyl)phenol; then condense it with ethyl(methyl)carbamic chloride before salifying it with L-(+)-tartaric acid to receive rivastigmine with the total yield of 18.73%.

WO2007025481 discloses a method: use S-phenethylamine as chiral pool to make key intermediate (S)-3-(1-(dimethylamino)ethyl)phenol with multi-step reactions; then condense it with ethyl(methyl)carbamic chloride before finally salifying it with L-(+)-tartaric acid to receive rivastigmine. Although the optical purity of the starting material is guaranteed, but they all require selective introduction of a functional group at the meta position of S-phenylethylamine, and the results are basically mixtures, which are difficult to purify.

The methods listed above either have a long resolution process with low yield, or difficulty to purify intermediates, which make them unsuitable for industrial production; plus the purity of the rivastigmine resulted cannot be guaranteed.

CONTENT OF THE DISCLOSURE

The present invention provides a novel formula IX compound with the following structure:

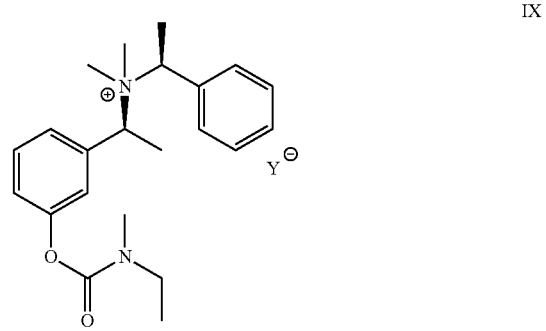

IX

Wherein Y is selected from halogen, $SO_4CH_3$, $CO_3CH_3$, $SO_3CF_3$ and $SO_3F$, preferably from Cl, Br, I, $SO_4CH_3$, $CO_3CH_3$.

The invention also provides a novel formula VIII compound with the following structure

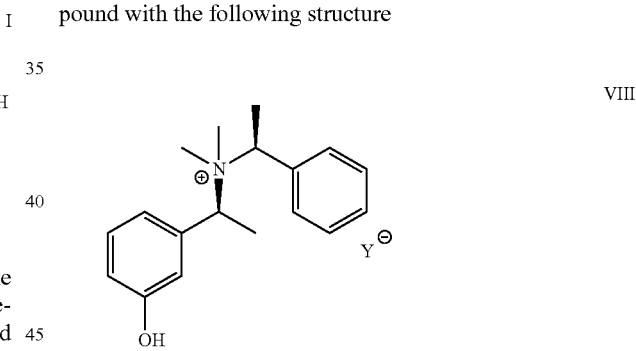

VIII

Wherein Y is selected from halogen, $SO_4CH_3$, $CO_3CH_3$, $SO_3CF_3$ and $SO_3F$, preferably from Cl, Br, I, $SO_4CH_3$, $CO_3CH_3$.

The present invention provides a novel formula VI compound with the following structure:

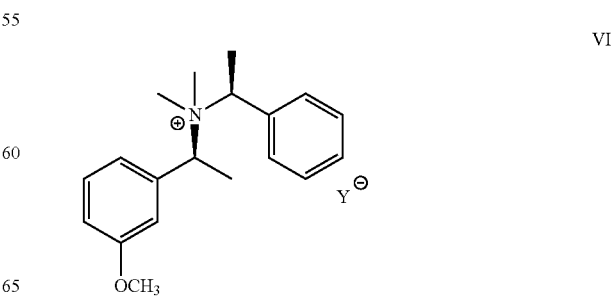

VI

Wherein Y is selected from halogen, SO₄CH₃, CO₃CH₃, SO₃CF₃ and SO₃F, preferably from Cl, Br, I, SO₄CH₃, CO₃CH₃.

Above mentioned formula VI compound, formula VIII compound and formula IX compound are the key intermediates for preparing formula X compound.

The present invention provides a method to prepare (S)-3-(1-(dimethylamino)ethyl)phenyl ethyl(methyl)carbamate (namely formula X) and tartaric acid salt (i.e. formula I), and the method includes:

a) First let formula IX compound undergo a debenzylation reaction to obtain formula X compound below:

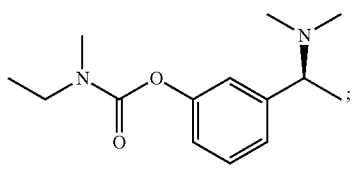

X b) formula X compound is then reacted with L-(+)-tartaric acid to receive formula I compound as below:

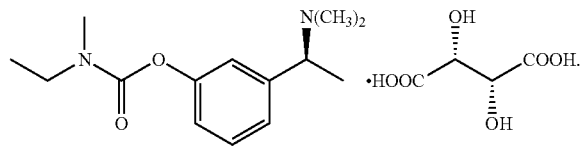

I

The said debenzylation reaction uses 2%-50% palladium-carbon catalyst; the reaction pressure is between 1-40 atm, preferably between 1-10 atm; reaction temperature is between 0° C. to 100° C., preferably between 0° C. to 40° C.; the alkaline substance used in the reaction is one or multiple substances from the following: inorganic basic compound (s) selected from sodium carbonate, potassium carbonate, sodium hydroxide, potassium hydroxide, sodium amide and sodium hydride; alkali metal alcoholate compound (s) selected from sodium methanol, sodium ethanol and potassium t-butoxide; organic basic compound (s) selected from triethylamine, pyridine, quinoline, diisopropyl ethyl amine, preferably sodium carbonate or potassium carbonate; organic solvent used in the reaction: alcohol solvent (s) selected from methanol, ethanol, propanol, isopropanol, butanol and tert-butanol; ether solvent (s) selected from diethyl ether, diisopropyl ether and tetrahydrofuran, or any mixture of above solvents, preferably methanol or ethanol.

The formula X compound in above reaction step b) and L-(+)-tartaric acid used to prepare formula I compound according to conventional method.

Formula IX compound in this invention can be prepared using the following four methods:

Method One:

a) formula V compound as below undergoes the methylation reaction to receive formula VIII compound;

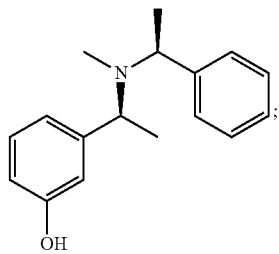

V b) formula VIII compound undergoes a condensation reaction with ethyl(methyl)carbamic chloride to obtain formula IX compound.

Method Two:

a) Formula III compound as shown below undergoes a methylation reaction to obtain formula VI compound:

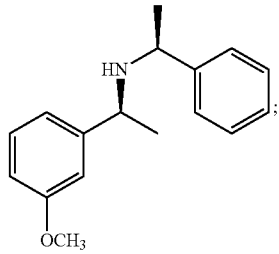

III b) Formula VI compound undergoes a demethylation reaction to obtain formula VIII compound;

c) Formula VIII compound undergoes a condensation reaction with ethyl(methyl)carbamic chloride to obtain formula IX compound.

Method Three:

a) Formula IV compound as shown below goes through a methylation reaction to obtain formula VI compound

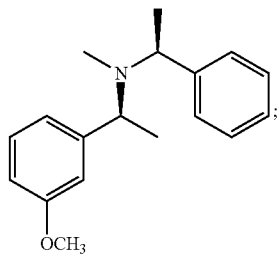

IV b) formula VI compound goes through the demethylation reaction to obtain formula VIII compound;

c) formula VIII compounds goes through a condensation reaction with ethyl(methyl)carbamic chloride to obtain formula IX compound.

Method Four:

a) formula V compound goes through a condensation reaction ethyl(methyl)carbamic chloride to obtain formula VII compound

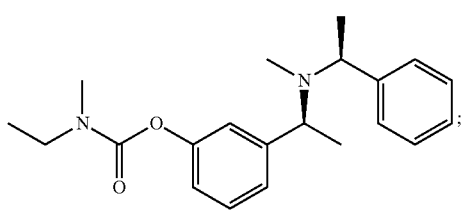

VII b) Formula (VII) compound goes through the methylation reaction to get formula IX compound.

Wherein said demethylation reaction may be conducted with the presence of hydrobromic acid, aluminum chloride, or concentrated sulfuric acid.

Wherein the methylation agent for said methylation reaction is selected from: fluoro methane, methyl chloride, methyl bromide, methyl iodide, dimethyl sulfate, dimethyl carbonate, methyl trifluoromethanesulfonate or methyl fluorosulfonate, preferably methyl chloride, methyl bromide, methyl iodide, dimethyl sulfate, dimethyl carbonate; said methylation reaction uses the reaction temperature of between 0° C. to 100° C., preferably between 40° C. to 80° C.; said methylation reaction uses an inert solvent as the reaction solvent, which includes but are not limited to: ether solvent (s) selected from tetrahydrofuran, diethyl ether, ethylene glycol dimethyl ether, dioxane and 2-methyltetrahydrofuran, aromatic hydrocarbon solvent (s) selected from benzene, toluene and xylene, halogenated hydrocarbon solvent (s) selected from dichloromethane, chloroform, and dichloroethane; alcohol solvent (s) from methanol, ethanol and isopropyl alcohol; amides solvent (s) selected from N,N-dimethylformamide and N,N-dimethylacetamide; as well as acetonitrile, ethyl acetate and acetone, and preferably N,N-dimethylformamide, N,N-dimethylacetamide amide or ethyl acetate.

Wherein said condensation reaction is added with alkaline substance (s), which are selected from one or more of the following substances: inorganic alkali compound (s) selected from sodium carbonate, potassium carbonate, sodium hydroxide, potassium hydroxide, sodium amide and sodium hydride; alkali metal alcoholate compound (s) selected from sodium methoxide, sodium ethoxide and potassium t-butoxide; organic base compound (s) selected from triethylamine, pyridine, quinoline and diisopropylethylamine, preferably sodium carbonate or potassium carbonate; said the condensation reaction temperature is between 0° C. to 120° C., preferably between 20° C. to 70° C.; the said condensation reaction uses an inert solvent as the reaction solvent, and said inert solvent includes but is not limited to: ether solvent (s) selected from tetrahydrofuran, diethyl ether, ethylene glycol dimethyl ether, dioxane and 2-methyl tetrahydrofuran; aromatic hydrocarbon solvent (s) selected from benzene, toluene and xylene; halogenated hydrocarbon solvent (s) selected from methylene dichloride, chloride and dichloroethane; alcohol solvent (s) selected from methanol, ethanol and isopropyl, as well as N, N-dimethylformamide, N,N-dimethylacetamide, acetonitrile, ethyl acetate and acetone, preferably acetonitrile; preferably phase transfer catalyst is added to the said condensation reaction, and said phase transfer catalysts includes but is not limited to: onium salt catalyst selected from tetrabutylammonium bromide, tetraethylammonium bromide, tetrabutylammonium iodide or triethyl benzyl ammonium chloride; open-chain polyether-based catalyst (s) selected from polyethylene glycol 400 (a generic term for polyethylene glycol having an average molecular weight of about 400 daltons), polyethylene glycol 600 (a generic term for polyethylene glycol having an average molecular weight of about 600 daltons) or polyethylene glycol 800 (a generic term for polyethylene glycol having an average molecular weight of about 800 daltons) as well as crown ether catalyst (s) selected from 12-crown-4, 15-crown-5 or 18-crown-6.

The synthetic process disclosed in this intention for preparing rivastigmine has a reasonable and simple design with convenient source of raw material. The total yield is high (≥45%), and the rivastigmine resulted has a high chemical and optical purity (HPLC purity greater than 99.8% while optical purity greater than 99.8%), which makes it easy for large-scale industrial production.

SPECIFIC EMBODIMENTS

This invention discloses Rivastigmine's preparation method, its intermediates and the intermediates' preparation method. Technicians in this field may take reference of what is described in this paper, appropriately improve the technical parameters and realize the process. What is noteworthy is that all such replacement and modifications are obvious to technicians in this field, which are covered in the scope of this invention. The methods of this invention have been described by good embodiments, and people in this field can apparently change, modify and combine the methods and applications described herein to realize and apply the invention herein and still stay within the scope of this invention's content and spirit.

In order to technicians in this field to better understand the technical plans of this invention, more detailed explanations are provided below with specific embodiments.

Please see below more detailed explanations along with specific embodiments, which do not constitute any restriction to the invention herein.

$^1$HNMR is recorded by an AM 400 nuclear magnetic resonance device, while chemical shift is expressed in δ (ppm), mass spectrometry measured by with a Shimadzu LCMS-2010 mass spectrometer, and optical rotation measured by a Perkin-Elmer 341 polarimeter.

Embodiment 1

Preparation of (S)-1-(3-methoxyphenyl)-N,N-dimethyl-N—((S)-1-phenylethyl)ethanaminium iodide (formula VI)

Mix 5.1 g (0.02 mol) of (S)-1-(3-methoxyphenyl)-N—((S)-1-phenylethyl)ethanamine (formula III) with 12 ml N,N-dimethylformamide, 14.2 g (0.1 mol) of methyl iodide and 2.7 g (0.02 mol) of potassium carbonate at room temperature, heat the mixture to 60° C. for 24 hours. After cooling it to room temperature, filter it, and add to the filtrate 100 ml of ethyl acetate, filter and dry the yellow solid produced and receive 6.2 g of the yellow solid with a yield of 75%.

$^1$HNMR (CDCl$_3$) δ: 2.05 (d, 3H), 2.08 (d, 3H), 2.88 (d, 6H), 3.85 (s, 3H), 5.16 (q, 1H), 5.18 (q, 1H), 6.94 (m, 1H), 7.25 (m, 2H), 7.42 (m, 4H), 7.78 (m, 2H); MS (ESI) m/z: 284.2 ([M-I]$^+$).

Embodiment 2

The preparation of (S)-1-(3-methoxyphenyl)-N,N-dimethyl-N—((S)-1-phenylethyl)ethanaminium bromide (formula VI)

Mix 5.1 g (0.02 mol) of (S)-1-(3-methoxyphenyl)-N—((S)-1-phenylethyl)ethanamine (formula III) with 12 ml N,N- dimethylformamide, 9.5 g (0.1 mol) of methyl bromide and 2.7 g (0.02 mol) of potassium carbonate at room temperature, heat the mixture to 60° C. for 24 hours. After cooling it to room temperature, filter and add 100 ml of ethyl acetate to the filtrate, a light yellow solid is produced. Filter and dry it to receive 5.2 g light yellow solid with a yield of 72%.

MS (ESI) m/z: 284.2 ([M-Br]$^+$).

Embodiment 3

Preparation of (S)-1-(3-methoxyphenyl)-N,N-dimethyl-N—((S)-1-phenylethyl)ethanaminium methyl sulfate (formula VI)

Mix 5.1 g (0.02 mol) of (S)-1-(3-methoxyphenyl)-N—((S)-1-phenylethyl)ethanamine (formula III) with 12 ml N,N-dimethylformamide, 12.6 g (0.1 mol) of dimethyl sulfate and 2.7 g (0.02 mol) of potassium carbonate at room temperature, heat the mixture to 60° C. for 24 hours. Let it cool to room temperature, filter and add 100 ml of ethyl acetate to the filtrate. A light yellow solid is produced. Filter and dry it to receive 5.5 g light yellow solid with a yield of 70%.

MS (ESI) m/z: 284.2 ([M-SO4CH3]$^+$)

Embodiment 4

The preparation of (S)-1-(3-methoxyphenyl)-N,N-dimethyl-N—((S)-1-phenylethyl)ethanaminium iodide (formula VI)

Mix 5.5 g (0.02 mol) of (S)-1-(3-methoxyphenyl)-N-methyl-N—((S)-1-phenylethyl)ethanamine (formula IV) with 12 ml N,N-dimethylformamide and 14.2 g (0.1 mol) of methyl iodide at room temperature, heat the mixture to 60° C. for 12 hours. Let it cool to room temperature, and add 100 ml of ethyl acetate. A yellow solid is produced. Filter and dry it to receive 5.8 g light yellow solid with a yield of 70%.

Embodiment 5

The preparation of (S)-1-(3-methoxyphenyl)-N,N-dimethyl-N—((S)-1-phenylethyl)ethanaminium bromide (formula VI)

Mix 5.5 g (0.02 mol) of (S)-1-(3-methoxyphenyl)-N-methyl-N—((S)-1-phenylethyl)ethanamine (formula IV) with 12 ml N,N-dimethylformamide and 9.5 g (0.1 mol) of methyl bromide at room temperature, heat the mixture to 60° C. for 24 hours. Let it cool to room temperature, and add 100 ml of ethyl acetate. A light yellow solid is produced. Filter and dry it to receive 5.0 g light yellow solid with a yield of 69%.

MS (ESI) m/z: 284.2 ([M-Br]$^+$).

Embodiment 6

The preparation of (S)-1-(3-methoxyphenyl)-N,N-dimethyl-N—((S)-1-phenylethyl)ethanaminium methyl sulfate (formula VI)

Mix 5.5 g (0.02 mol) of (S)-1-(3-methoxyphenyl)-N-methyl-N—((S)-1-phenylethyl)ethanamine (formula IV) with 12 ml N,N-dimethylformamide and 12.6 g (0.1 mol) of dimethyl sulfate at room temperature, heat the mixture to 60° C. for 24 hours. Let it cool to room temperature, and add 100 ml of ethyl acetate. A light yellow solid is produced. Filter and dry it to receive 5.7 g light yellow solid with a yield of 72%.

MS (ESI) m/z: 284.2 ([M-SO4CH3]$^+$).

Embodiment 7

The preparation of (S)-1-(3-hydroxyphenyl)-N,N-dimethyl-N—((S)-1-phenylethyl)ethanaminium iodide (formula VIII)

Mix 8.2 g (0.02 mol) of (S)-1-(3-methoxyphenyl)-N,N-dimethyl-N—((S)-1-phenylethyl)ethanaminium iodide (formula VI) with 15 ml (content greater than 40% by mass) hydrobromic acid, heat and reflux the mixture for 10 hours. Let it cool to room temperature, and add 120 ml of acetone. A pale yellow solid is produced. Filter and dry it to receive 6.4 g pale yellow solid with a yield of 80%.

$^1$HNMR (DMSO) δ: 1.81 (d, 3H), 1.84 (d, 3H), 2.60 (s, 6H), 4.91 (q, 1H), 4.99 (q, 1H), 6.90 (m, 1H), 7.03 (s, 1H), 7.10 (d, 1H), 7.30 (t, 1H), 7.51 (t, 3H), 7.69 (m, 2H), 9.71 (s, 1H);

MS (ESI) m/z: 270.2 ([M-I]$^+$).

Embodiment 8

The preparation of(S)-1-(3-hydroxyphenyl)-N,N-dimethyl-N—((S)-1-phenylethyl)ethanaminium iodide (formula VIII)

Mix 5.1 g (0.02 mol) of 3-[(S)-1-(methyl-[(S)-1-phenylethyl]amino)ethyl]phenol (formula V) with 10 ml N,N-dimethylformamide and 11.3 g (0.08 mol) of methyl iodide at room temperature, heat the mixture to 55° C. and let it react for 5 hours. Cool it to room temperature and add 100 ml of ethyl acetate. A yellow solid is produced. Filter and dry it to receive 7.5 g yellow solid with a yield of 94%.

Embodiment 9

The preparation of (S)-1-(3-hydroxyphenyl)-N,N-dimethyl-N—((S)-1-phenylethyl)ethanaminium bromide (formula VIII)

Mix 5.1 g (0.02 mol) of 3-[(S)-1-(methyl-[(S)-1-phenylethyl]amino)ethyl]phenol (formula V) with 10 ml N,N-dimethylformamide and 7.5 g (0.08 mol) of methyl bromide at room temperature, and heat the mixture to 60° C. for 10 hours. Let it cool to room temperature and add 100 ml of ethyl acetate. A light yellow solid is produced. Filter and dry it to receive 6.5 g light yellow solid with a yield of 89%.

MS (ESI) m/z: 270.2 ([M-Br]±).

Embodiment 10

The preparation of (S)-1-(3-hydroxyphenyl)-N,N-dimethyl-N—((S)-1-phenylethyl)ethanaminium methyl sulfate (formula VIII)

Mix 5.1 g (0.02 mol) of 3-[(S)-1-(methyl-[(S)-1-phenylethyl]amino)ethyl]phenol (formula V) with 10 ml N,N-dimethylformamide and 12.6 g (0.1 mol) of dimethyl sulfate at room temperature, and heat the mixture to 60° C. for 10 hours. Let it cool to room temperature, and add 100 ml of ethyl acetate. A light yellow solid is produced. Filter and dry it to receive 7.0 g light yellow solid with a yield of 85%.

MS (ESI) m/z: 270.2 ([M-SO$_4$CH$_3$]$^+$).

Embodiment 11

The preparation of (S)-1-(3-hydroxyphenyl)-N,N-dimethyl-N—((S)-1-phenylethyl)ethanaminium iodide (formula VIII)

Mix 5.1 g (0.02 mol) of 3-[(S)-1-(methyl-[(S)-1-phenylethyl]amino)ethyl]phenol (formula V) with 20 ml of ethyl acetate and 11.3 g (0.08 mol) of methyl iodide at room temperature, and heat the mixture to 60° C. for 10 hours. After cooling it to room temperature, filter and dry it to obtain 7.0 g yellow solid with a yield of 88%.

Embodiment 12

The preparation of (S)-1-(3-hydroxyphenyl)-N,N-dimethyl-N—((S)-1-phenylethyl)ethanaminium iodide (formula VIII)

Mix 5.1 g (0.02 mol) of 3-[(S)-1-(methyl-[(S)-1-phenylethyl]amino)ethyl]phenol (formula V) with 10 ml of methanol and 11.3 g (0.08 mol) of methyl iodide at room temperature, and heat the mixture to 60° C. for 10 hours. Cool it to room temperature and add 100 ml of ethyl acetate. A yellow solid is produced. Filter and dry it to receive 6.9 g yellow solid with a yield of 87%.

Embodiment 13

The preparation of (S)-1-(3-(ethyl(methyl)carbamoyloxy)phenyl)-N,N-dimethyl-N—((S)-1-phenylethyl)ethanaminium iodide (formula IX)

Dissolve 5 g (0.02 mol) of 3-[(S)-1-(methyl-[(S)-1-phenylethyl]amino)ethyl]phenol (formula V) in 50 ml of acetone, and add 3.5 g (0.025 mol) of potassium carbonate and 3.1 g (0.025 mol) ethyl(methyl)carbamic chloride. Reflux and stir it for 15 hours before reducing the pressure to recover the solvent. Then add 60 ml of water and extract it twice with 100 ml ethyl acetate, combine the organic layers, and wash it twice with 30 ml 0.1N aqueous sodium hydroxide solution, then wash it twice with 20 ml of water. Dry with anhydrous magnesium sulfate, reduce the pressure to recovered the solvent and receive 8.0 g liquid.

The above colorless liquid is mixed with 10 ml N,N-dimethylformamide and 14.2 g (0.1 mol) of methyl iodide at room temperature. The mixture is heated to 60° C. for 10 hours before cooling down to room temperature. Then the pressure is reduced to recover the solvent and receive 10.0 g of red-brown liquid to be directly used in the next reaction.

$^1$HNMR (CDCl$_3$) δ: 1.18 (m, 3H), 2.01 (d, 3H), 2.07 (d, 3H), 2.85 (d, 6H), 2.93, 3.05 (2×s, 3H), 3.35, 3.46 (2×q, 2H), 5.18 (q, 1H), 5.22 (q, 1H), 7.20 (m, 1H), 7.43 (m, 5H), 7.73 (m, 2H), 7.81 (m, 1H);

MS (ESI) m/z: 355.4 ([M-I]$^+$).

Embodiment 14

The preparation of (S)-1-(3-(ethyl(methyl)carbamoyloxy)phenyl)-N,N-dimethyl-N—((S)-1-phenylethyl)ethanaminium iodide (formula IX)

Mix 7.9 g (0.02 mol) (S)-1-(3-hydroxyphenyl)-N,N-dimethyl-N—((S)-1-phenylethyl)ethanaminium iodide (formula VIII) with 180 ml of acetonitrile, 4.1 g (0.03 mol) of potassium carbonate, 3.6 g (0.03 mol) ethyl(methyl)carbamic chloride and 0.1 g of macrogol 400 at room temperature, heat the mixture to 60° C. and let it react for 12 hours. After cooling to room temperature, filter it and reduce the pressure to recover the solvent and receive 10.3 g of red-brown liquid to be directly used in the next reaction.

Embodiment 15

The preparation of (S)-1-(3-(ethyl(methyl)carbamoyloxy)phenyl)-N,N-dimethyl-N—((S)-1-phenylethyl)ethanaminium iodide (formula IX)

Mix 7.9 g (0.02 mol) (S)-1-(3-hydroxyphenyl)-N,N-dimethyl-N—((S)-1-phenylethyl)ethanaminium iodide (formula VIII) with 180 ml of acetonitrile, 4.1 g (0.03 mol) of potassium carbonate, 3.6 g (0.03 mol) ethyl(methyl)carbamic chloride and 0.1 g of macrogol 400 at room temperature, let it react at 20° C. for 16 hours. Filter it and reduce the pressure to recover 9.8 g of red-brown liquid to be directly used in the next reaction.

Embodiment 16

The preparation of (S)-1-(3-(ethyl(methyl)carbamoyloxy)phenyl)-N,N-dimethyl-N—((S)-1-phenylethyl)ethanaminium iodide (formula IX)

Mix 7.9 g (0.02 mol) of(S)-1-(3-hydroxyphenyl)-N,N-dimethyl-N—((S)-1-phenylethyl)ethanaminium iodide (formula VIII) with 180 ml of acetonitrile, 4.1 g (0.03 mol) of potassium carbonate, 3.6 (0.03 mol) ethyl(methyl)carbamic chloride and 0.1 g of tetrabutylammonium bromide at room temperature, heat it to 60° C. and react it for 12 hours. After it is cooled to room temperature, filter it and reduce the pressure to recover the solvent and receive 9.5 g of red-brown liquid to be directly used in the next reaction.

Embodiment 17

The preparation of (S)-1-(3-(ethyl(methyl)carbamoyloxy)phenyl)-N,N-dimethyl-N—((S)-1-phenylethyl)ethanaminium iodide (formula IX)

Mix 7.9 g (0.02 mol) of(S)-1-(3-hydroxyphenyl)-N,N-dimethyl-N—((S)-1-phenylethyl)ethanaminium iodide (formula VIII) with 180 ml of acetonitrile, 4.1 g (0.03 mol) of potassium carbonate, 3.6 g (0.03 mol) ethyl(methyl)carbamic chloride chloride and 0.1 g 18-crown-6 at room temperature, heat it to 60° C. and react it for 12 hours. After it is cooled to room temperature, filter it and reduce the pressure to recover the solvent and receive 9.9 g of red-brown liquid to be directly used in the next reaction.

Embodiment 18

The preparation of (S)-1-(3-(ethyl(methyl)carbamoyloxy)phenyl)-N,N-dimethyl-N—((S)-1-phenylethyl)ethanaminium iodide (formula IX)

Mix 7.9 g (0.02 mol) of (S)-1-(3-hydroxyphenyl)-N,N-dimethyl-N—((S)-1-phenylethyl)ethanaminium iodide (formula VIII) with 100 ml of methanol, 4.1 g (0.03 mol) of potassium carbonate, 3.6 g (0.03 mol) ethyl(methyl)carbamic chloride and 0.1 g of macrogol 400 at room temperature, heat it to 60° C. and react it for 12 hours. After it is cooled to room temperature, filter it and reduce the pressure to recover the solvent and receive 9.0 g of red-brown liquid to be directly used in the next reaction.

Embodiment 19

The preparation of (S)-1-(3-(ethyl(methyl)carbamoyloxy)phenyl)-N,N-dimethyl-N—((S)-1-phenylethyl)ethanaminium iodide (formula IX)

Mix 7.9 g (0.02 mol) of (S)-1-(3-hydroxyphenyl)-N,N-dimethyl-N—((S)-1-phenylethyl)ethanaminium iodide (formula VIII) with 180 ml of acetonitrile, 1.7 g (0.03 mol) of potassium hydroxide, 3.6 (0.03 mol) ethyl(methyl)carbamic chloride and 0.1 g of macrogol 400 at room temperature, heat it to 60° C. and react it for 12 hours. After it is cooled to room temperature, filter it and reduce the pressure to recover the solvent and receive 10.2 g of red-brown liquid to be directly used in the next reaction.

Embodiment 20

The preparation of (S)-3-(1-(dimethylamino)ethyl) phenyl ethyl(methyl)carbamate (formula X)

Mix 10 g (0.02 mol) of (S)-1-(3-(ethyl(methyl)carbamoyloxy)phenyl)-N,N-dimethyl-N—((S)-1-phenylethyl)ethanaminium iodide (formula IX) obtained in Embodiment 14 with 100 ml of methanol, 4.1 g (0.03 mol) of potassium carbonate, 2 g Pd/C (10% mass), and add the mixture to a 250 ml hydrogenation reactor, set 5 atm, and let it react for 8 hours when the internal temperature is 20° C. Open the reactor and obtain the mixture. Filter out Pd/C, reduced pressure to recover the solvent. Then add 50 ml of water before adding carbonate sodium in portions while adjusting pH to 8. Extracted with ethyl acetate (60 ml×2), combine the organic layer and wash it with 15 ml of water. Dry with anhydrous magnesium sulfate and filter, and reduce the pressure to recover the solvent and receive 6.5 g pale yellow liquid.

Distillation under reduced pressure: 1-1.5 kpa, collect the 128-133° C. fraction 4.3 g, yield 85%.

Optical rotation $[\alpha]20D=-32.1°$ (C=5, ethanol).
$^1$HNMR (CDCl$_3$) δ ppm: 1.22 (m, 3H), 1.35 (q, 3H), 2.20 (s, 6H), 3.02 (d, 3H), 3.25 (m, 1H), 3.44 (s, 2H), 7.05 (m, 3H), 7.27 (m, 1H); MS (ESI) m/z: 251.2 ([M+1]$^+$).

Embodiment 21

The preparation of (S)-3-(1-(dimethylamino)ethyl) phenyl ethyl(methyl)carbamate (formula X)

Mix 10 g (0.02 mol) of(S)-1-(3-(ethyl(methyl)carbamoyloxy)phenyl)-N,N-dimethyl-N—((S)-1-phenylethyl)ethanaminium iodide (formula IX) obtained in Embodiment 14 with 100 ml of methanol, 4.1 g (0.03 mol) of potassium carbonate and 0.5 g Pd/C (10% mass), and add the mixture to a 250 ml hydrogenation reactor, set 1 atm, and let it react for 8 hours when the internal temperature is 20° C. Open the reactor and obtain the mixture. Filter out Pd/C, reduced pressure to recover the solvent. Then add 50 ml of water before adding carbonate sodium in portions while adjusting pH to 8. Extracted with ethyl acetate (60 ml×2), combine the organic layer and wash it with 15 ml of water. Dry with anhydrous magnesium sulfate and filter, and reduce the pressure to recover the solvent and receive 6.3 g pale yellow liquid.

Distillation under reduced pressure: 1-1.5 kpa, collecting the 128-133° C. fraction 4.1 g, yield 82%.

Optical rotation $[\alpha]^{20}_D=-32.1°$ (C=5, ethanol).

Embodiment 22

The Preparation of Rivastigmine (Formula I)

Mix 5.0 g (0.02 mol) (S)-3-(1-(dimethylamino)ethyl)phenyl ethyl(methyl)carbamate (formula X) with 20 ml acetone and 3.0 g L-tartaric acid (0.02 mol) at room temperature, heat the mixture until it refluxes, and let it react for 40 min. After it is cooled to 40° C., add seed crystals and stir it at room temperature for 2 hours. Use ice bath for insulation for 5 hours and set it in a refrigerator overnight. Filter it, and set it in a vacuum oven at 40° C. for 10 hours to receive 6.64 g white crystals with a yield of 83%.

HPLC purity≥99.8%, ee value of ≥99.8%.

Optical rotation $[\alpha]^{20}_D=+6.0°$ (C=5, ethanol); mp 123.8-124.5° C.

$^1$HNMR (CDCl$_3$) δ: 1.16, 1.24 (2×t, 3H), 1.67 (d, 3H), 2.65 (s, 6H), 2.96, 3.05 (2×s, 3H), 3.37, 3.45 (2×q, 2H), 4.34 (q, 1H), 4.47 (s, 2H), 7.14 (t, 1H), 7.20 (s, 1H), 7.28 (d, 1H), 7.39 (t, 1H);

MS (ESI) m/z: 251.2 ([M+1]$^+$).

Rivastigmine's preparation method, its intermediates and the intermediates' preparation method disclosed in this invention has been described in embodiments. It is apparent that related technicians can change, modify or combine Rivastigmine's preparation method, its intermediates and the intermediates' preparation method as described herein to realize the technology involved in this invention within the scope of this invention's content and spirit. What is noteworthy is that all such similar replacement and modifications are obvious to technicians in this field, which are covered in the scope of this invention's content and spirit.

The invention claimed is:

1. A compound corresponding to Formula IX:

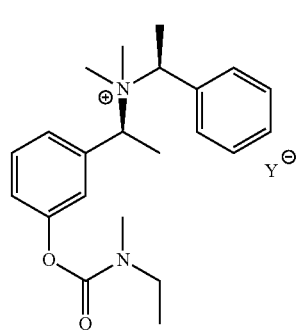

Formula IX wherein Y is selected from the group consisting of SO$_4$CH$_3$, CO$_3$CH$_3$, SO$_3$CF$_3$, SO$_3$F, Cl, Br, and I.

2. A compound corresponding to Formula VIII:

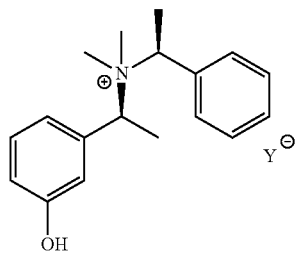

Formula VIII wherein Y is selected from the group consisting of SO₄CH₃, CO₃CH₃, SO₃CF₃, SO₃F, CI, Sr, and I.

3. A compound corresponding to formula VI:

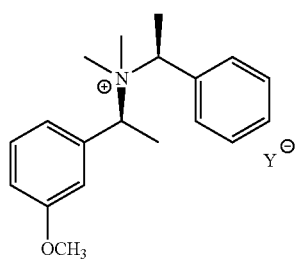

Formula VI wherein Y is selected from the group consisting of SO₄CH₃, CO₃CH₃, SO₃CF₃, SO₃F, CI, Br, and I.

4. A method for preparing the compound corresponding to formula IX as described in claim 1, the method comprising:
methylating a compound corresponding to formula V to obtain a compound corresponding to formula VIII,
wherein the compound of formula V corresponds to:

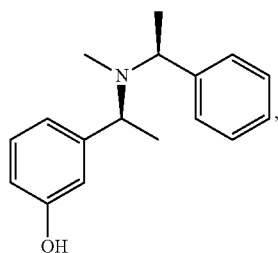

Formula V wherein the compound of formula VIII corresponds to:

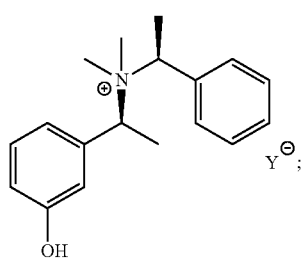

Formula VIII and allowing the compound corresponding to formula VIII to undergo a condensation reaction with ethyl(methyl)carbamic chloride to obtain the compound corresponding to formula IX,
wherein the compound of formula IX corresponds to:

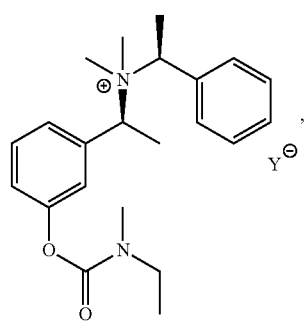

Formula IX wherein Y is selected from the group consisting of SO₄CH₃, CO₃CH₃, SO₃CF₃, SO₃F, CI, Br, and I.

5. A method for preparing a compound corresponding to formula IX, the method comprising:
methylating a compound of formula III to obtain a compound corresponding to formula VI,
wherein the compound of formula III corresponds to:

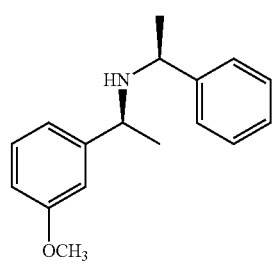

Formula III wherein the compound of formula VI corresponds to:

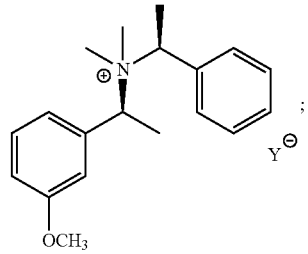

Formula VI demethylating a compound corresponding to formula VI to obtain a compound comes to formula VIII;

wherein the compound of formula VIII corresponds to:

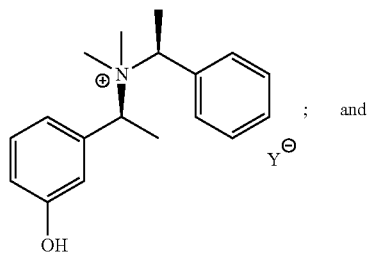

Formula VIII

; and performing a condensation reaction between the compound corresponding formula VIII and ethyl(methyl)carbamic chloride to obtain a compound corresponding formula IX, wherein the compound of formula IX corresponds to:

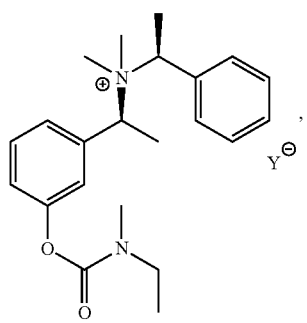

Formula IX

, wherein Y is selected from the group consisting of SO₄CH₃, CO₃CH₃; SO₃CF₃, SO₃F, Cl, Br, and I.

6. A method for preparing a compound corresponding to formula IX, the method comprising:

methylating a compound corresponding to formula IV to obtain a compound corresponding to formula VI wherein the compound of formula IV corresponds to:

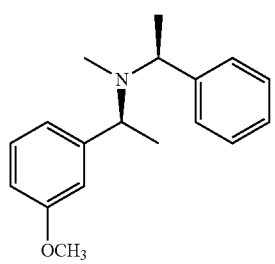

Formula IV wherein the compound of formula VI corresponds to:

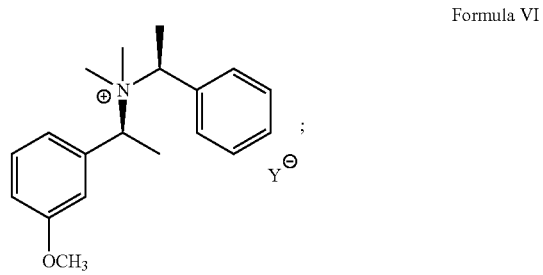

Formula VI

;

demethylating the compound corresponding to formula VI to obtain a compound corresponding to formula VIII, wherein the compound of formula VIII corresponds to:

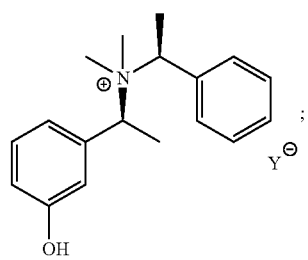

Formula VIII

;

and performing a condensation reaction between the compound corresponding to formula VIII and ethyl(methyl)carbamic chloride to obtain a compound corresponding to formula IX, wherein the compound of formula IX corresponds to:

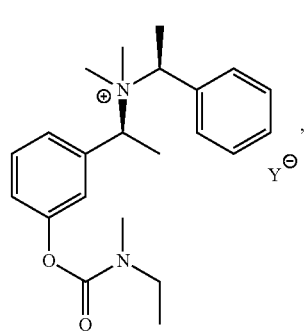

Formula IX

, wherein Y is selected from the group consisting of SO₄CH₃, CO₃CH₃, SO₃CF₃, SO₃F, Cl, Br, and I.

7. A method for preparing a compound corresponding to formula IX, the method comprises:

performing a condensation reaction between a compound corresponding to formula V with ethyl(methyl)carbamic chloride to obtain a compound corresponding to formula VII, wherein the compound of formula V corresponds to:

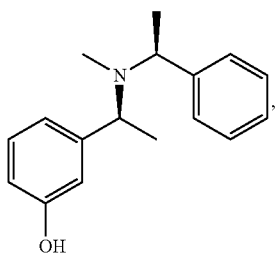

Formula V wherein the compound of formula VII corresponds to:

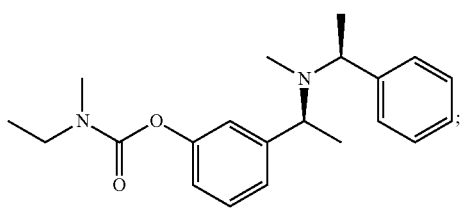

Formula VII and
methylating the compound corresponding to formula VII to obtain a compound corresponding to formula IX
wherein the compound of formula IX corresponds to:

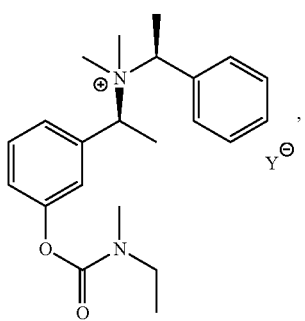

Formula IX wherein Y is selected from the group consisting of $SO_4CH_3$, $CO_3CH_3$, $SO_3CF_3$, $SO_3F$, Cl, Br, and I.

8. The method according to any one of claims 5 and 6, wherein demethylation is performed in the presence of hydrobromic acid, aluminum chloride or concentrated sulfuric acid.

9. The method according to any one of the claims 4-7,
wherein the methylation agents are selected from the group consisting of methyl fluoride, methyl chloride, methyl bromide, methyl iodide, dimethyl sulfate, dimethyl carbonate, methyltrifluoromethane sulfonate, and methyl fluorosulfonate;

wherein the methylation is performed between 0° C.-100° C.;

wherein methylation uses an inert solvent as a reaction solvent in which the inert solvent is selected from the group consisting of an ether solvent, an aromatic hydrocarbon solvent, a halogenated hydrocarbon solvent, an alcohol solvent, an amide solvent, acetonitrile, ethyl acetate, and acetone;

wherein the ether solvent is selected from the group consisting of tetrahydrofuran, diethyl ether, ethylene glycol dimethyl ether, dioxane, and 2-methyltetrahydrofuran;

wherein the aromatic hydrocarbon solvent is selected from the group consisting of benzene, toluene, and xylene;

wherein the halogenated hydrocarbon solvent is selected from the group consisting of dichloromethane, chloroform, and dichloroethane;

wherein the alcohol solvent is selected from the group consisting of methanol, ethanol, and isopropanol; and wherein the amide solvent is selected from the group consisting of N,N-dimethylformamide, and N,N-dimethylacetamide.

10. The method according to any one of claims 4-6, wherein at least one of an alkaline substance is added to the condensation reaction in which the alkaline substance is selected from the group consisting of an inorganic alkali compound, an alkali metal alcoholate compound, and an organic alkali compound;

wherein the inorganic alkali compound is selected from the group consisting of sodium carbonate potassium carbonate, sodium hydroxide, potassium hydroxide, sodium amide, and sodium hydride;

wherein the alkali metal alcoholate compound is selected from the group consisting of sodium methylate, sodium ethoxide, and potassium tert-butoxide; and wherein the organic alkali compound is selected from the group consisting of triethylamine, pyridine, quinoline, and diisopropyl ethyl amine;

wherein the condensation reaction temperature is between 0° C.-120° C.;

wherein the condensation reaction uses an inert solvent as the reaction solvent in which the inert solvent is selected from the group consisting of an ether solvent, an aromatic hydrocarbon solvent, a halogenated hydrocarbon solvent, an alcohol solvent, an amide solvent, acetonitrile, and acetone;

wherein the ether solvent is selected from the group consisting of tetrahydrofuran, diethyl ether, ethyl glycol dimethyl ether, dioxane, and 2-methyl tetrahydrofuran;

wherein the aromatic hydrocarbon solvent is selected from the group consisting of benzene, toluene, and xylene;

wherein the halogenated hydrocarbon solvent is selected from the group consisting of dichloromethane, chloroform, and dichloroethane;

wherein the alcohol solvent is selected from the group consisting of methanol, ethanol, and isopropanol;

wherein the amide solvent is selected from the group consisting of N, N-dimethylformamide, and N, N-dimethylacetamide;

wherein a phase transfer catalyst is added in the condensation reaction in which the phase transfer catalyst is selected from the group consisting of onium salt catalyst, open-chain polyether catalyst, and crown ether catalyst;- wherein the onium salt catalyst is selected from tetrabutylammonium bromide, tetraethylammonium bromide, tetrabutyl ammonium iodide and triethyl benzyl ammonium chloride;

wherein the open-chain polyether catalyst is selected from the group consisting of polyethylene glycol 400, polyethylene glycol 600, and polyethylene glycol 800; and wherein the crown ether catalyst is selected from the group consisting of 12-crown-4, 15-crown-5, and 18-crown-6.

11. A method for preparing a compound ERA corresponding to formula I, the method comprising;

debenzylating a compound of formula IX to obtain a compound of formula X, wherein the compound of formula I corresponds to:

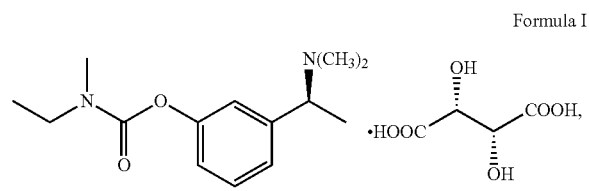

Formula I wherein the compound of formula IX corresponds to:

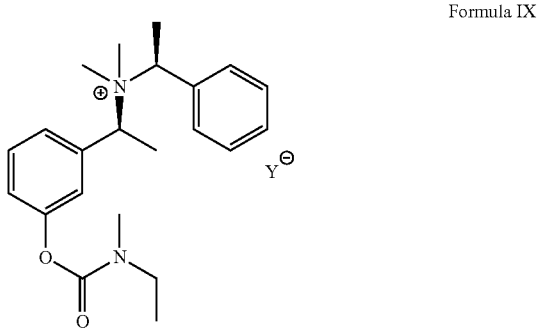

Formula IX wherein the compound of formula X corresponds to:

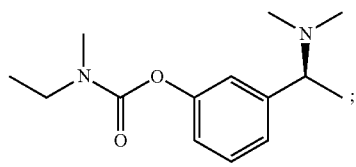

Formula X and reacting a compound corresponding to formula X with L-(+)-tartaric acid to obtain a compound of formula I.

12. The method of claim 11, wherein the debenzylation reaction uses 2%-50% palladium-carbon catalyst at a reaction pressure between 1-40 atm and at a reaction temperature of between 0° C.-100° C., and at least one of the alkaline substance used in the debenzylation is selected from the group consisting of an inorganic basic compound, an alkali metal alcohol compound, and an organic alkali compound;

wherein the inorganic basic compound is selected from the group consisting of sodium carbonate, potassium carbonate, sodium hydroxide, potassium hydroxide, sodium amide, and sodium hydride;

wherein the alkali metal alcoholate compound is selected from the group consisting of sodium methoxide, sodium ethoxide, and potassium tert-butoxide;

wherein the organic basic compound is selected from the group consisting of triethylamine, pyridine, quinoline, and diisopropyl ethylamine;

wherein the organic solvent used in the debenzylation reaction is selected from the group consisting of an alcohol solvent, an ether solvent and mixtures thereof;

wherein alcohol solvent is selected from the group consisting of propanol, methanol, ethanol, isopropanol, butanol, and tert-butanol;

wherein the ether solvent is selected from the group consisting of diethyl ether, diisopropylether, and tetrahydrofuran.

* * * * *